(12) United States Patent
Beckett et al.

(10) Patent No.: US 10,132,762 B2
(45) Date of Patent: Nov. 20, 2018

(54) ADAPTER FOR MEASURING INSTRUMENT

(71) Applicant: JOHNSON MATTHEY PUBLIC LIMITED COMPANY, London (GB)

(72) Inventors: Oliver John Beckett, County Durham (GB); Brian Wilson, Stockton-on-Tees (GB)

(73) Assignee: Johnson Matthey Public Limited Company, London, England (GB)

( * ) Notice: Subject to any disclaimer, the term of this patent is extended or adjusted under 35 U.S.C. 154(b) by 215 days.

(21) Appl. No.: 15/107,030

(22) PCT Filed: Dec. 18, 2014

(86) PCT No.: PCT/GB2014/053768
§ 371 (c)(1),
(2) Date: Jun. 21, 2016

(87) PCT Pub. No.: WO2015/097452
PCT Pub. Date: Jul. 2, 2015

(65) Prior Publication Data
US 2016/0349194 A1 Dec. 1, 2016

(30) Foreign Application Priority Data

Dec. 23, 2013 (GB) .................................. 1322944.8
Aug. 4, 2014 (GB) .................................. 1413804.4

(51) Int. Cl.
*G01N 23/18* (2018.01)
*G01N 23/046* (2018.01)

(52) U.S. Cl.
CPC ........... *G01N 23/18* (2013.01); *G01N 23/046* (2013.01); *G01N 2223/3303* (2013.01); *G01N 2223/628* (2013.01)

(58) Field of Classification Search
CPC ........... G01N 23/18; G01N 2223/3303; G01N 2223/628; G01N 9/24; G01N 2223/419;
(Continued)

(56) References Cited

U.S. PATENT DOCUMENTS 3,835,324 A 9/1974 Weigle
5,614,720 A 3/1997 Morgan et al.
(Continued)

FOREIGN PATENT DOCUMENTS

EP 2 470 077 B1 1/2015
GB 2 211 708 A 7/1989
(Continued)

OTHER PUBLICATIONS

International Search Report, dated Mar. 31, 2015, from corresponding PCT Application.

*Primary Examiner* — Courtney Thomas
(74) *Attorney, Agent, or Firm* — Baker & Hostetler LLP

(57) ABSTRACT

An adapter apparatus includes a generally cylindrical adapter body 14 including a channel 16 extending axially therethrough, the adapter body having an interior surface, bounding the channel, and an exterior surface 18, a generally circular external cross section and an interior cross section which is adapted to engage at least one object 10, the external surface being formed from a material which is capable of supporting a scanning or testing apparatus at a constant distance from the origin of the circle forming the external cross section.

15 Claims, 1 Drawing Sheet

(58) Field of Classification Search
CPC ..... G01N 23/046; G01T 1/2018; G01T 1/164; G21K 1/02
See application file for complete search history.

(56) References Cited

U.S. PATENT DOCUMENTS

| | | |
|---|---|---|
| 2003/0142783 A1 | 7/2003 | Daaland et al. |
| 2006/0048589 A1 | 3/2006 | Lavoie |
| 2012/0033788 A1* | 2/2012 | Kovarik ................ B66F 11/042 378/58 |

FOREIGN PATENT DOCUMENTS

| | | |
|---|---|---|
| WO | 2008/127074 A1 | 10/2008 |
| WO | 2013/064838 A1 | 5/2013 |
| WO | WO 2015/024080 A1 | 2/2015 |

* cited by examiner

ADAPTER FOR MEASURING INSTRUMENT

The present invention concerns apparatus for scanning or otherwise testing vessels or pipes, optionally in water, for example, but not limited to, scanning or measurement instruments for use in sub-sea environments.

A particular method of scanning pipelines, which may be underwater, was described in WO2013/064838. In that method a source of gamma radiation and an array of radiation detectors is rotated around a part to be scanned, such as a pipeline. The detector array is precisely arranged relative to the source so that the scanning can be carried out at high resolution. Such precision apparatus is large and expensive to build. It is therefore advantageous to be able to use it for scanning a variety of parts, for example pipelines of different dimensions or for arrangements in which the vessel or pipeline does not present a circular cross-section. One example of such a situation arises where a first pipeline has a second pipeline or other structure located close to the first pipeline, possibly extending along the route of the first pipeline or for at least a part of its length. Such an arrangement creates a problem in attaching and operating a scanning apparatus which is intended to scan around the circumference of the first pipeline. It is an object of the present invention to provide an apparatus which overcomes this problem.

According to the invention, an adapter apparatus comprises a generally cylindrical adapter body including a channel extending axially therethrough, said adapter body having an interior surface bounding said channel and an exterior surface, a generally circular external cross section and an interior cross section which is adapted to engage at least one vessel or pipeline, the external surface being formed from a material which is capable of supporting a scanning or testing apparatus at a constant distance from the origin of the circle forming the external cross section.

The exterior surface is formed from a material which is capable of supporting a scanning or testing apparatus at a constant distance from the origin of the circle forming the external cross section. This means that the material forming the external surface does not deform significantly when a scanning or testing apparatus is mounted on said adapter or when said scanning or testing apparatus is operated in accordance with its usual mode of operation. The scanning instrument described in WO2013/064838, for example, is rotated around a vessel or pipeline in its usual mode of operation. An adapter apparatus for use with such a scanning instrument would therefore be resistant to deformation when such an instrument is mounted on it and rotated around the adapter. The material is preferably durable and resistant to the conditions in which it is used. A suitable material for the adapter body, or at least the external surface thereof, comprises a metal or a polymeric material such as polyethylene, of sufficient thickness to provide the necessary resistance to deformation. The adapter is preferably capable of maintaining its shape when subjected to hydrostatic compression, which is experienced when it is to be attached around a vessel located in or under water. Therefore a rigid polymeric or metal shell may be preferred for such applications.

The adapter body may be formed from a single material or may comprise different material. The adapter body may comprise an external wall or skin within which is provided a second material to fill the space within the external skin. The second material may be more dense or less dense that the skin material. The second material may be selected to have a density which provides an adapter body of a particular density so that the weight or buoyancy of the adapter body may be selected to be appropriate for the particular application, for example to facilitate handling and manoeuvring of the adapter body. The adapter body may comprise more than two materials within a skin or shell. The adapter body may comprise an external skin material surrounding a void, optionally filled with a gas or liquid.

The exterior surface of the adapter body is adapted to engage a scanning or testing apparatus for scanning or testing a pipe or vessel with which the interior surface is designed to engage. The exterior surface may be smooth or contoured. The exterior surface may include contours or profiles which are adapted to engage with a scanning apparatus. The contours may engage with a scanning apparatus in a manner which affects the operation of the scanning apparatus. The exterior surface of the adapter body may provide a means by which a scanning apparatus may be moved axially along said adapter body. The exterior surface of the adapter body may comprise surface contours which engage a movement means in such a way that the movement means is guided to move in a particular direction. Surface contours of the exterior surface of the adapter may engage a movement means in such a way that the movement means is guided to move a particular distance. The exterior surface may comprise surface contours which provide an indexing means for a movement means with which said contours may be engaged. For example the exterior surface may comprise a plurality of ribs which are spaced a predetermined distance apart and which provide an indexing means for movement which traverses more than one said rib. Ribs may extend circumferentially around the exterior surface of said adapter body. Ribs may extend longitudinally along the exterior surface. Ribs may extend longitudinally in a direction which is not parallel to the longitudinal axis of the adapter body.

The exterior surface of the adapter may comprise indicia such as identification codes, a measurement scale or numbering. The exterior surface of the adapter may comprise one or more position transducers. A position transducer may be used to enable the scanning apparatus to determine its position along an adapter body and thereby determine its location with respect to the vessel or pipeline.

The interior surface of said adapter body surrounds a channel extending longitudinally through the adapter body. The interior surface has a cross section which may be circular or part circular. When the interior cross section is circular the adapter body may be described as toroidal. The cross section may alternatively be of a different shape in order to accommodate different shapes of vessels or pipelines to be scanned. The interior cross section is shaped to adapt to the shape of a vessel or pipeline which is to be scanned. When, for example, two pipes are run generally parallel and close together and it is desirable to scan at least one of those pipes, the adapter body has an interior cross section into which both pipes may fit. In such a case the interior cross section of the adapter body may be generally circular over a substantial part, the circular section being sized to fit around one said pipe, with an additional space intersecting a part of the edge of the cross section into which may be fitted the second pipe.

The interior surface may be of a size and shape to fit closely around the surface of the vessel to be scanned. Alternatively the interior surface may be adapted to engage a smaller proportion of the surface of the vessel to be scanned, for example up to about 80% of the surface. The interior surface may comprise longitudinal channels so that projections from the vessel may be accommodated. When the adapter is used in water, the channels may prevent the formation of a vacuum around the vessel which may otherwise cause difficulty when the adapter is removed.

The interior surface may be adapted to engage with inserts or blocks which fit between the interior of the adapter and the vessel or pipeline. Such inserts or blocks may be used when the channel extending through the adapter is too large to engage the vessel.

The interior surface may comprise a material which is compliant or deformable. Such a material may be used in order to reduce the risk of damaging the surface of the vessel when the adapter is engaged thereon. The compliant material may be provided as a layer covering the whole or a part of the interior surface of the adapter. Suitable materials include synthetic or natural rubbers and other elastomers. The compliant material may provide a means by which the adapter may engage different vessels of slightly different dimensions.

The adapter comprises means by which it may be fitted around the vessel or pipeline. The adapter may be provided in two or more portions which may be assembled around the vessel to form a complete adapter. The portions may be joined together by joining means which may include conventional joining equipment such as clamps, straps, bolts, latches or screws. One or more of the portions may be provided with one or more lugs or projections which engage with one or more recesses Or channels provided in one or more other portions when the portions are correctly located to be joined together. The adapter may be split longitudinally into two portions which are rotatably joined or hinged along an edge to provide a "clamshell" type of arrangement. The adapter may then be positioned around the vessel when the clamshell is open and then closed around the vessel. The closure may comprise joining means such as those already described.

The adapter may be provided in modular lengths, which may be joined together to form a longer length of adapter. Each modular length may be provided with a means to engage with and be joined to an adjacent modular length. Each modular length may be provided with one or more lugs or projections which engage with one or more recesses or channels provided in another modular length when adjacent modular lengths are correctly located to be joined together. By providing an adapter of the invention in modular form, the adapter may be transported, manoeuvred and fitted more easily. Furthermore a modular adapter enables an adapter of a desired length to be formed from shorter length. The adapter modules may be supplied in standard lengths. The modular lengths may be joined by a joining means comprising a means, such as a spring, for compressing adjacent modular lengths together to maintain them in a fixed position relative to each other.

The adapter body may be manufactured as a unit. The adapter may alternatively be manufactured as modules which are subsequently joined together to form a complete adapter body or a modular length. The modules may be joined together by means of clamps, bolts, straps, tiebars or alternative joining means. The modules may be joined by a joining means comprising a means, such as a spring, for compressing adjacent modules together to maintain the modules in a fixed position relative to each other.

The adapter may comprise means for engaging with a remotely operated vehicle (ROV). The adapter may comprise handles for holding and manipulating the adapter into position. The adapter may comprise at least one anchoring position which may be used to anchor an ROV in a fixed position relative to the adapter.

The external diameter of the adapter is sized to fit to or within the scanning apparatus. The channel extending through the adapter is sized to fit around the object or vessel to be scanned. The adapter may be fixed to the object to be scanned, for example by means of one or more clamps or cables. The adapter may be fitted to the object to be scanned before the scanning operation has begun. The adapter may be removed from the object or moved to a different part of the object when the scanning operation is completed.

A method of scanning an object according to an embodiment of the invention may therefore comprise the steps of attaching to the object an adapter then placing a scanning apparatus adjacent said adapter and carrying out a scanning operation using said scanning apparatus. The object may comprise a vessel or pipeline.

The scanning or measuring apparatus may use the detection of radiation passing through the object in order to generate scanning data. In such a case, the materials used to form the adapter advantageously do not attenuate, reflect or absorb such radiation in such a way as to interfere with the scanning operation. Whilst the use of some components which attenuate radiation may be unavoidable, it is preferred that a substantial part of the adapter body is formed from a material which is not significantly more attenuating to the radiation used than is water.

The scanning apparatus may comprise a pipe-scanning apparatus of the type described in WO2013/064838. Alternatively the scanning apparatus may comprise a different apparatus in which radiation is used to estimate the density along a path through an object or structure. As a further alternative, the scanning or testing apparatus may comprise a different type of apparatus in which radiation is not used.

An example incorporating several optional features of the invention will be described with reference to the appended drawings.

Figure 1:
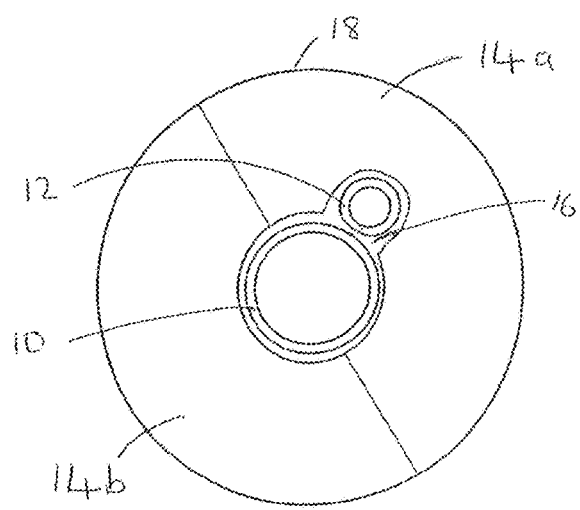
FIG. 1 is a sectional schematic view of a section of a pair of pipes enclosed within an adapter of the invention.
Figure 2:
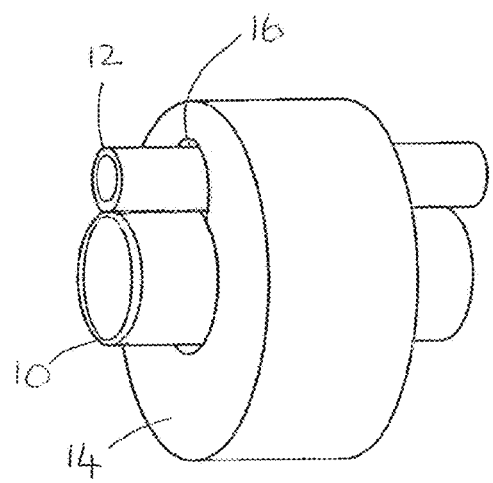
FIG. 2 is a schematic perspective view of the arrangement shown in FIG. 1.

FIGS. 1 and 2 show a pipeline 10 and a second pipeline 12 fitted with an adapter 14. The adapter is made from high density polyethylene (HDPE). The adapter 14 is formed of two portions 14a and 14b which are joined together so as to enclose the pipes 10,12 within a channel 16 extending through the adapter. The channel is shaped to accommodate both of the pipes. In this way a circular surface is provided by the exterior surface 18 of the adapter for the scanning apparatus to bear upon and move around, even though the pipes which are to be scanned do not, together provide such a surface which the scanning apparatus could use. The outside diameter of the adapter is selected to fit into a scanning apparatus. The scanning apparatus is placed over the adapter 14 before the scanning operation is started. The adapter 14 may be removed or moved to a different portion of pipeline when the scanning operation is complete.

Figure 3:
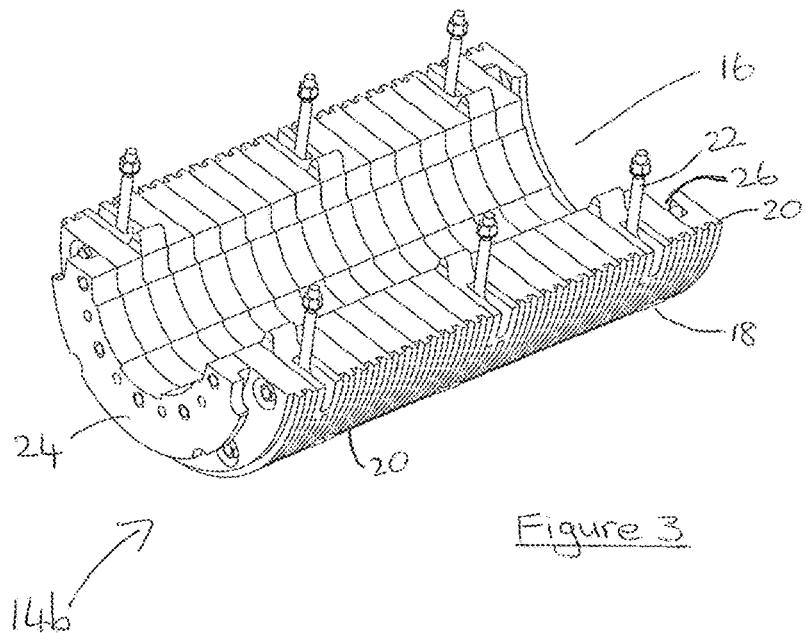
FIG. 3 is a view of a portion of an adapter according to the invention.

FIG. 3 shows a portion 14b of an adapter in more detail. The adapter portion is hemicylindrical and is intended to form a complete cylinder when joined to a second hemicylindrical adapter portion. The exterior surface is provided with ribs 20 which extend around the adapter. When the adapter portion is joined to a second hemicylindrical adapter portion the ribs extend around the circumference of the cylinder formed. Two portions of the adapter are joined by means of swing bolts 22. One end of the adapter portion is provided with a protruding portion 24 and the other is provided with a recess 26. When the protruding portion of one adapter is located in the recess of a second adjacent adapter, the two may be joined together to provide a continuous length of adapter. The adapter is designed so that the ribs are evenly spaced and that the rib spacing is maintained across two adapters when they are joined together. In this way, the adapter is modular.

The invention claimed is:

1. An adapter apparatus comprising a generally cylindrical adapter body including a channel extending axially therethrough, said adapter body having an interior surface bounding said channel, and an exterior surface, a generally circular external cross section and an interior cross section which is adapted to engage at least one object, the external surface being formed from a material which is capable of supporting a scanning or testing apparatus at a constant distance from the origin of the circle forming the external cross section, and wherein the exterior surface comprises a plurality of ribs which are spaced apart.

2. The adapter apparatus according to claim 1, wherein the adapter body comprises at least one material within a skin or shell formed of a different material.

3. The adapter apparatus according to claim 1, wherein the exterior surface is smooth or contoured.

4. The adapter apparatus according to claim 1, wherein the exterior surface provides a means by which a scanning apparatus may be moved axially along said adapter body.

5. The adapter apparatus according to claim 1, wherein said ribs extend circumferentially around the exterior surface of said adapter body.

6. The adapter apparatus according to claim 1, wherein said ribs extend longitudinally along the exterior surface.

7. The adapter apparatus according to claim 1, wherein the interior surface of said adapter body has a circular cross section.

8. The adapter apparatus according to claim 1, wherein the interior surface of said adapter body has a non-circular cross section.

9. The adapter apparatus according to claim 1, further comprising inserts or blocks which are adapted to fit between the interior surface of the adapter and the object to be scanned.

10. The adapter apparatus according to claim 1, wherein the interior surface comprises a material which is compliant or deformable.

11. The adapter apparatus according to claim 1, wherein the adapter comprises two or more portions which may be assembled around the object to form a complete adapter.

12. The adapter apparatus according to claim 1, comprising at least two modular lengths, which may be joined together to form a longer length of adapter.

13. A method of scanning an object comprising the steps of attaching an adapter to the object then placing a scanning apparatus adjacent an external surface of said adapter and carrying out a scanning operation using said scanning apparatus, wherein said adapter is an adapter according to claim 1.

14. The method according to claim 13, wherein said scanning operation involves causing radiation to pass through said object and detecting a portion of said radiation.

15. The adapter apparatus according to claim 2, wherein the exterior surface is smooth or contoured.

* * * * *